United States Patent
Ogawa

(10) Patent No.: US 6,881,189 B2
(45) Date of Patent: *Apr. 19, 2005

(54) ULTRASONIC RECEIVING APPARATUS AND ULTRASONIC RECEIVING METHOD

(75) Inventor: Eiji Ogawa, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/390,928

(22) Filed: Mar. 19, 2003

(65) Prior Publication Data

US 2003/0184753 A1 Oct. 2, 2003

(30) Foreign Application Priority Data

Mar. 26, 2002 (JP) ......................................... 2002-084971

(51) Int. Cl.[7] .................................................. A61B 8/14

(52) U.S. Cl. ....................................... 600/459; 600/472

(58) Field of Search .......................... 600/437, 441–447, 600/472, 476; 73/601–633; 367/149; 356/477, 479, 502; 348/493, 769; 359/1, 7, 30, 32; 342/179

(56) References Cited

U.S. PATENT DOCUMENTS 6,709,393 B1 * 3/2004 Ogawa ........................ 600/443

FOREIGN PATENT DOCUMENTS

| DE | 43 09 056 A | 9/1994 |
|---|---|---|
| EP | 1 156 345 A | 11/2001 |
| WO | WO 01/50100 A | 7/2001 |

OTHER PUBLICATIONS

Takahashi et al., Underwater Acoustic Sensor with Fiber Bragg Grating, Optical Review, vol. 4, No. 6 (1997),p. 694.
Uno et al., Fabrication and Performance of a Fiber Optic Micro–Probe for Megahertz Ultrasonic Field Measurements, T.IEE Japan, vol. 118–E, No. 11, 1998, p. 487–p. 492.
Beard et al., Transduction Mechanisms of the Fabry–Perot Polymer Film Sensing Concept for Wideband Ultrasound Detection, IEEE Transactions on Ultrasonics. Ferroelectrics, and Frequency Control, vol. 46, Nov. 1999, p. 1575–p1582.
Wilkens V et al: "Optical Multilayer Detection Array for Fast Ultrasonic Field Mapping" Optics Letters, Optical Society of America, Aug. 1, 1999: 1026–1028; XP000973108 ISSN: 0146–9592: vol. 25, No. 15: US Washington,

* cited by examiner

*Primary Examiner*—Ali Imam
(74) *Attorney, Agent, or Firm*—Sughrue Mion, PLLC

(57) ABSTRACT

An ultrasonic receiving apparatus capable of reducing changes in detection sensitivity due to environmental changes such as temperature and the variations of detection sensitivity depending upon the positions in the ultrasonic detecting element. The ultrasonic receiving apparatus includes: a light source for generating broadband light; an ultrasonic detecting element including an ultrasonic sensing portion which is expanded and contracted by a received ultrasonic wave to change an optical reflectance thereof in accordance with expansion and contraction thereby performing intensity modulation of the light generated by the light source; a spectrum separating unit for spectrum-separating the light intensity-modulated by the ultrasonic detecting element; and photodetector having a plurality of photoelectric converting elements for detecting the light spectrum-separated by the spectrum separating unit for each of plural wavelength components.

7 Claims, 10 Drawing Sheets

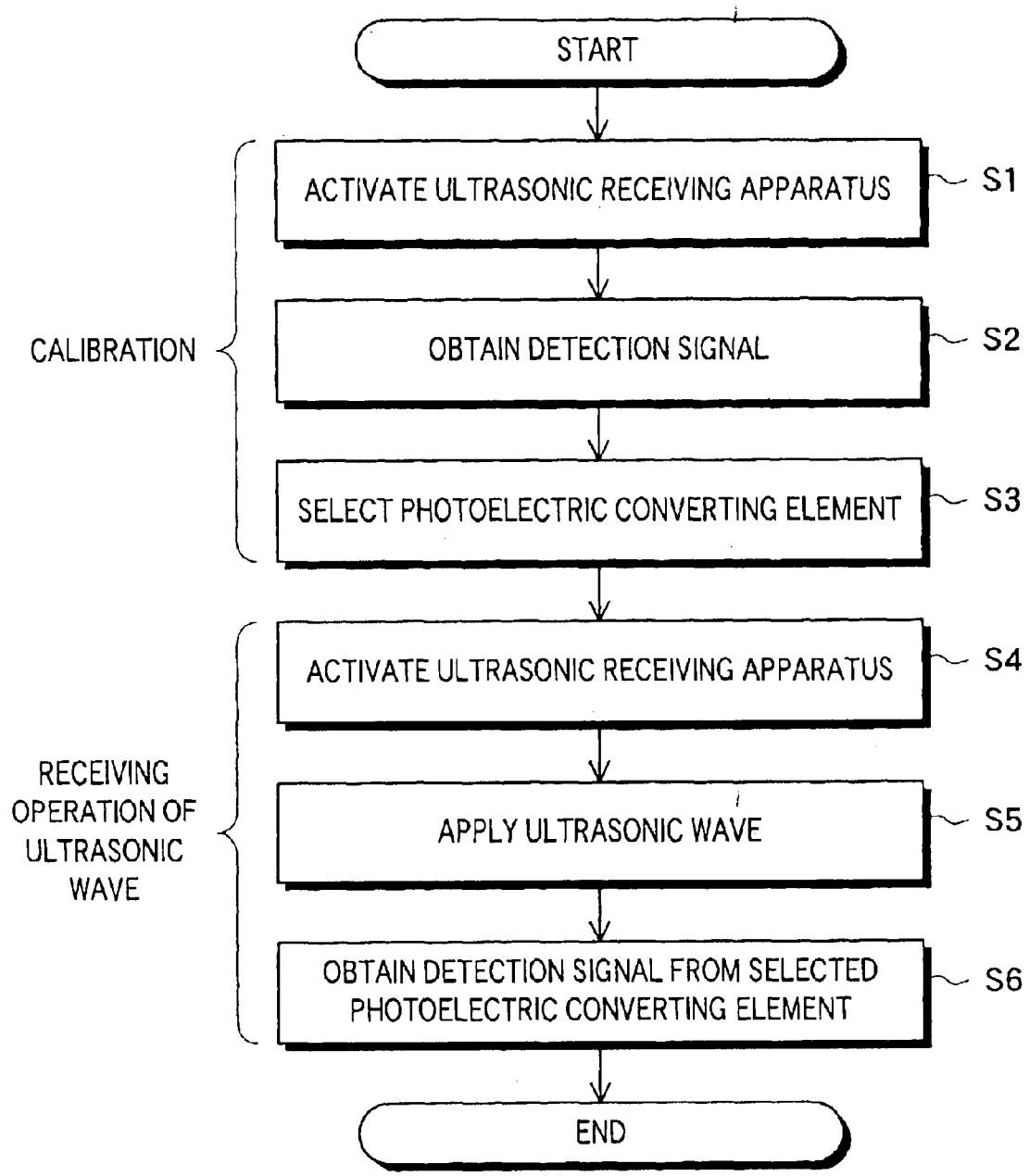

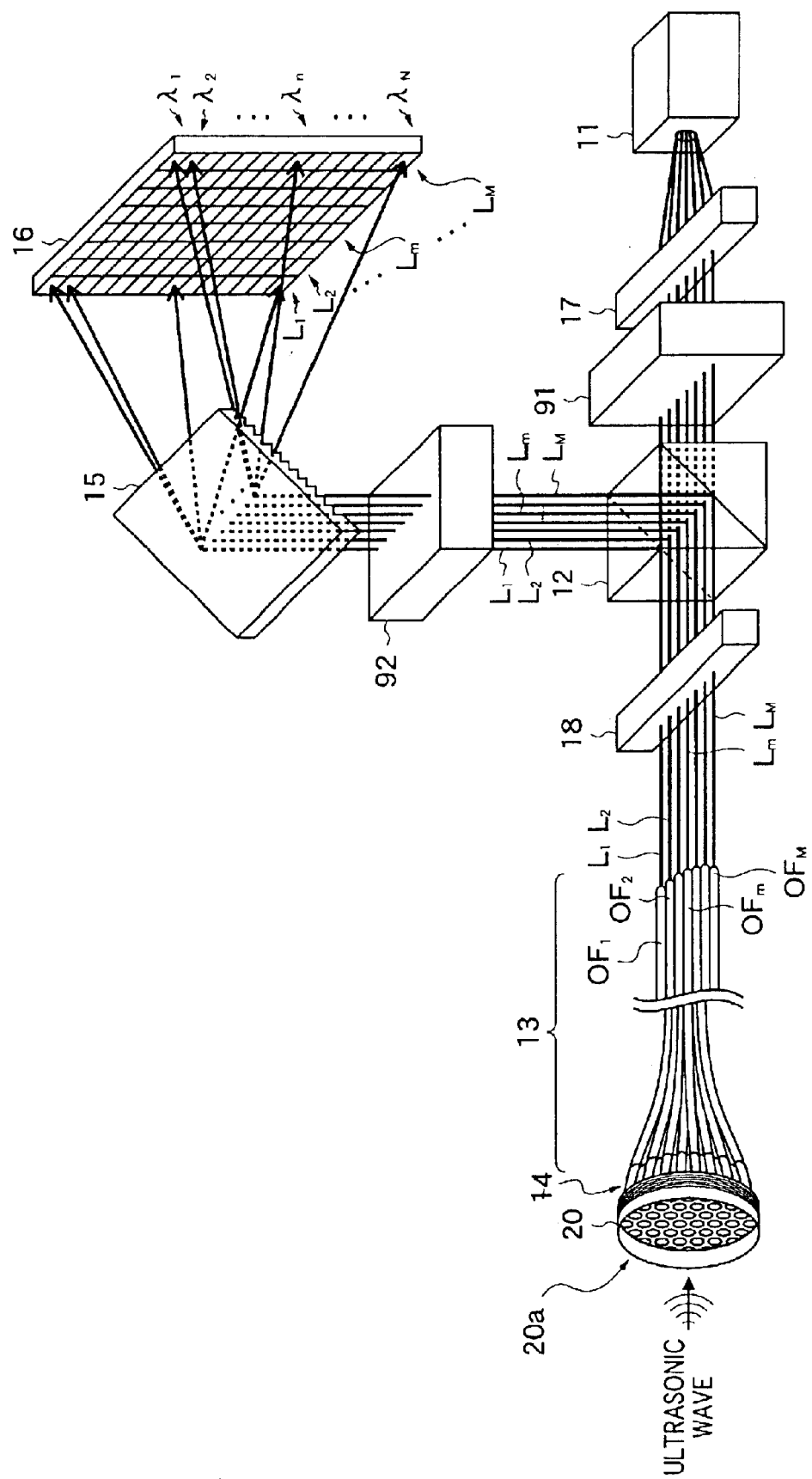

ULTRASONIC RECEIVING APPARATUS AND ULTRASONIC RECEIVING METHOD

BACKGROUND OF THE INVENTION

1. Field of the Invention

The present invention relates to an ultrasonic receiving apparatus and an ultrasonic receiving method for obtaining ultrasonic images by receiving ultrasonic waves.

2. Description of a Related Art

Conventionally, in an ultrasonic imaging apparatus, a one-dimensional sensor array using a piezoelectric element that includes a piezoelectric ceramic represented by PZT (Pb(lead) zirconate titanate) or a macromolecule piezoelectric element such as PVDF (polyvinylidene difluoride) has been generally used as an element (oscillator) for sending and receiving ultrasonic waves. Two-dimensional images in plural cross sections of an object to be inspected are obtained while mechanically shifting the one-dimensional sensor array above, and further, a three-dimensional-image is obtained by synthesizing these two-dimensional images.

However, according to this technique, since a time lag is generated in the shifting direction of the one-dimensional sensor array, cross-sectional images taken at different times are synthesized resulting in a blurred synthesized image. Therefore, the technique is not suitable for taking images of a living organism as an object in ultrasonic echo observation etc. using the ultrasonic imaging apparatus.

In order to obtain high quality three-dimensional images using ultrasonic waves, a two-dimensional sensor capable of obtaining two-dimensional images without shifting the sensor array is required.

If the two-dimensional sensor array is manufactured using PZT or PVDF as above, micro-processing on elements and wiring to a large number of micro-elements are required. However, it is difficult to achieve further miniaturization and integration of elements with the current technology. Even though the difficulties could be overcome, such problems still remain that crosstalk between elements increases, electrodes of microelements become easily broken, and SN-ratio becomes lower due to increase of electric impedance caused by micro-wirings. Therefore, it is difficult to apply the two-dimensional sensor array using PZT or PVDF in practice.

On the other hand, another type of sensor is also known. In a photo-detection type ultrasonic sensor, a received ultrasonic wave signal is converted into an optical signal and detected. As the photo-detection type ultrasonic sensor, a sensor in which a fiber Bragg grating (abbreviated as FBG) is used (see TAKAHASHI et al., National Defense Academy "Underwater Acoustic Sensor with Fiber Bragg Grating", OPTICAL REVIEW Vol.4, No.6 (1997), pp. 691–694), and a sensor in which a Fabry-Perot resonator (abbreviated as FPR) structure is used (see UNO et al., Tokyo Institute of Technology "Fabrication and Performance of a Fiber Optic Micro-Probe for Megahertz Ultrasonic Field Measurement", T.IEE Japan, Vol. 118-E, No.11, 1998, pp. 487–492) are reported. Manufacturing a two-dimensional sensor array by using those ultrasonic sensors provides the advantages that electrical wiring to a large number of microelements is not required and satisfactory sensitivity can be obtained.

Further, a photo-detection system ultrasonic sensor having a two-dimensional detection surface is also known. For example, Beard et al., University College London "Transduction Mechanisms of the Fabry-Perot Polymer Film Sensing Concept for Wideband Ultrasound Detection" (IEEE TRANSACTIONS ON ULTRASONICS, FERROELECTRICS, AND FREQUENCY CONTROL, VOL. 46, NO. 6, NOVEMBER 1999, pp. 1575–1582) discloses that a polymer film having a Fabry-Perot structure is used for detecting ultrasonic waves. In the film-like ultrasonic sensor, the cost can be reduced since processing on a large number of micro-elements is not required.

In either case, the photo-detection type ultrasonic sensor utilizes an ultrasonic detecting element having optical reflection characteristics that change by receiving ultrasonic waves. However, in the ultrasonic detecting element, the detection sensitivity widely varies since the optical reflection characteristics also change due to changes in temperature and humidity. Further, in the ultrasonic detecting element having a two-dimensional detecting surface, the detection sensitivity varies since the optical reflection characteristics differ in respective positions on the detecting surface. As described above, the problem in practical use of the photo-detection type ultrasonic sensor is how to control changes in detection sensitivity caused by environmental factors such as temperature and structural factors. For this purpose, a conceivable solution is, for example, to adjust the wavelength of the light output from the light source to the point where the sensitivity of the ultrasonic detecting element is high, however, it is difficult to tune the wavelength of the light of the light source with respect to the reflection characteristics that change very steeply. Another conceivable solution is to allow broadband light to enter the ultrasonic detecting element having different reflection characteristics in its respective positions and filter the reflected light, however, in this case, the constitution of the ultrasonic detecting element becomes complicated and the cost rises. Yet another conceivable solution is to vary the reflection characteristics for respective detection areas of the ultrasonic detecting element, however, also in this case, the constitution of the ultrasonic detecting element becomes complicated and the cost rises.

SUMMARY OF THE INVENTION

The invention has been achieved in view of the above-described problems. An object of the invention is, in an ultrasonic receiving apparatus and a ultrasonic receiving method using a photo-detection system, to reduce changes in the detection sensitivity to ultrasonic waves caused by environmental changes such as changes in temperature and variations in the detection sensitivity depending on positions in the ultrasonic detecting element, and to cut down on costs by simplifying the constitution of the apparatus.

In order to solve the above-described problems, an ultrasonic receiving apparatus according to the invention comprises: a light source for generating broadband light; an ultrasonic detecting element including an ultrasonic sensing portion which is expanded and contracted by a received ultrasonic wave to change an optical reflectance thereof in accordance with expansion and contraction thereby performing intensity modulation of the light generated by the light source; spectrum separating means for spectrum-separating the light intensity-modulated by the ultrasonic detecting element; and photo detecting means having a plurality of photoelectric converting elements for detecting the light spectrum-separated by the spectrum separating means for each of plural wavelength components.

Further, an ultrasonic receiving method according to the invention comprises the steps of: (a) allowing light to enter an ultrasonic detecting element including an ultrasonic sensing portion which is expanded and contracted by a received ultrasonic wave to change an optical reflectance thereof in response to the expansion and contraction thereby performing intensity modulation of the incident light, spectrum-separating the light intensity-modulated in a plurality of detection areas of the ultrasonic detecting element and detecting the spectrum-separated light for each of plural wavelength components by using photo detecting means having a plurality of photoelectric converting elements so as to obtain relationship between wavelengths and reflection intensity of the light in a plurality of detection areas of an ultrasonic detecting element; (b) selecting a set of photoelectric converting elements to be used for detecting an ultrasonic wave from among the plurality of photoelectric converting elements of the detecting means on the basis of the relationship obtained at step (a); and (c) allowing light to enter the ultrasonic detecting element when receiving the ultrasonic wave, outputting the light intensity-modulated by a received ultrasonic wave in the ultrasonic detecting element into different directions depending upon the wavelengths thereof and detecting the light for each of plural wavelength components by using the set of photoelectric converting elements selected at step (b) so as to obtain information on the ultrasonic wave received in the plurality of detection areas of the ultrasonic detecting element.

According to the invention, the relationship between wavelengths and reflection intensity of light can be obtained in the plural detection areas of the ultrasonic detecting element by spectrum-separating the light reflected in the ultrasonic detecting element and allowing the light to enter the different photoelectric converting elements. In addition, the detection signal can be obtained according to the light that has the optimum wavelength, by selecting photoelectric converting elements used when receiving ultrasonic waves on the basis of the relationship in advance.

BRIEF DESCRIPTION OF THE DRAWINGS

FIG. 5 is a flowchart showing an operation of the ultrasonic receiving apparatus according to the first embodiment of the invention;

FIG. 9 is a view showing a modification of the ultrasonic receiving apparatus according to the first and second embodiments of the invention;

DESCRIPTION OF THE PREFERRED EMBODIMENTS

Figure 1:
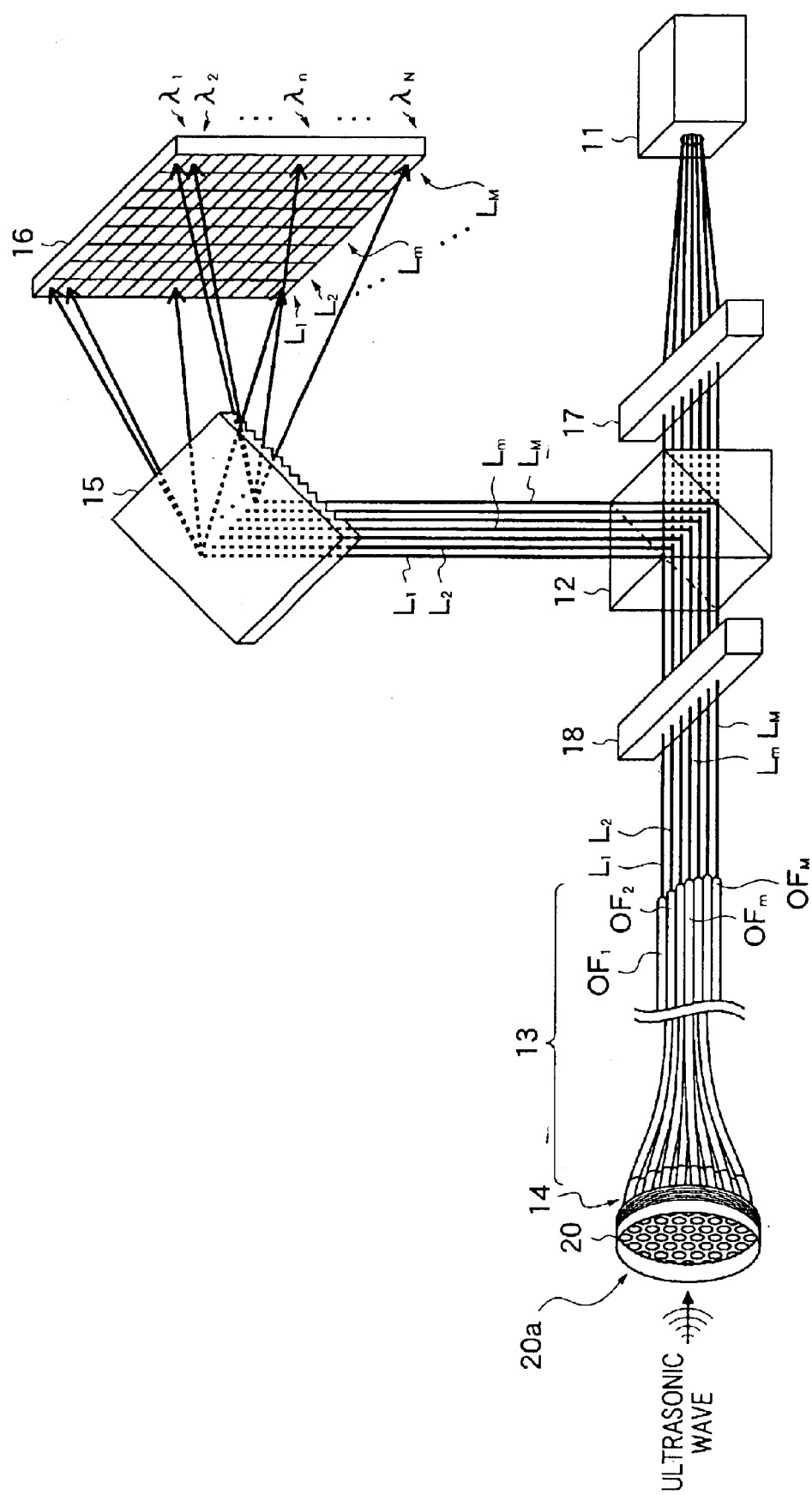
FIG. 1 is a diagram showing a constitution of an ultrasonic receiving apparatus according to a first embodiment of the invention.

Now, referring to the drawings, embodiments of the invention will be described in detail. The same component elements will be given with the same reference numerals and the descriptions thereof will be omitted.

FIG. 1 is a diagram showing an ultrasonic receiving apparatus according to a first embodiment of the invention. The ultrasonic receiving apparatus comprises a light source 11, a beam separator 12, an optical transmission path 13, a collimating portion 14, an ultrasonic detecting element 20, a spectrum-separating element 15, a photodetector 16, and collimator lenses 17 and 18.

In the following description, the relationship between wavelengths and reflection intensity of light in the ultrasonic detecting element 20 is referred to as "reflection characteristics".

As the light source 11, it is desirable to use one having a bandwidth that can cover a wider range over an inclined band in the reflection characteristics of the ultrasonic detecting element. The light source such as an LED (light emitting diode), an SLD (super luminescent diode), an ASE (amplified spontaneous emission) light source, or an LD (laser diode) having a larger line width is used.

The beam separator 12 comprises a half mirror, a light circulator, a polarizing beam splitter, etc. The beam separator 12 allows incident light entered from a first direction to pass through in a second direction, and reflects the light returned from the second direction in a third direction which is different from the first direction. In the embodiment, a half mirror is used as the beam separator 12. The half mirror allows the incident light to transmit in a direction opposite to the incident direction, and reflects the light returned from the direction opposite to the incident direction, in a direction substantially at an angle of 90° with the incident direction.

The optical transmission path 13 guides the light, which has passed through the beam separator 12, to the ultrasonic detecting element 20. As the optical transmission path 13, a bundle fiber, in which a large number of optical fibers (for example, 1,024 fibers) are bundled, is used. FIG. 1 shows optical fibers $OF_1$–$OF_M$ arranged in a line. As shown in FIG. 1, the large number of optical fibers are bundled into a configuration in accordance with a form of a receiving surface (a circular configuration, for example) on a side of the ultrasonic detecting element (on the left side in the drawing), and arranged in a line on a side of the beam separator 12 (on the right side in the drawing). Alternatively, plural rows of optical fibers arranged in a line may be stacked one another.

The front end of the optical transmission path 13 is connected to the ultrasonic detecting element 20 via the collimating portion 14 with the optical axes thereof aligned with each other. The collimating portion 14 includes, for example, a collimator lens array in which a plurality of collimator lenses are arrayed. The constitution of the optical transmission path 13 and the collimating portion 14 will be described in detail later.

The ultrasonic detecting element 20 has a two-dimensional receiving surface 20a that is distorted by a propagating ultrasonic wave, and an ultrasonic sensing portion that expands and contracts according to the ultrasonic wave received by the receiving surface 20a. Since an optical reflectance of the ultrasonic sensing portion changes in response to the expansion and contraction, the light that has entered the ultrasonic detecting element 20 via the optical transmission path 13 and the collimating portion 14 is subjected to intensity modulation and then reflected.

The spectrum-separating element 15 comprises a diffraction grating, a prism, etc. and outputs the incident light in directions that differ according to the wavelength. The spectrum-separating element 15 spectrum-separates light beams $L_1$–$L_M$ output in parallel from the optical fibers $OF_1$–$OF_M$ and guides the spectrum-separated light beams to the photodetector 16.

Figure 2:
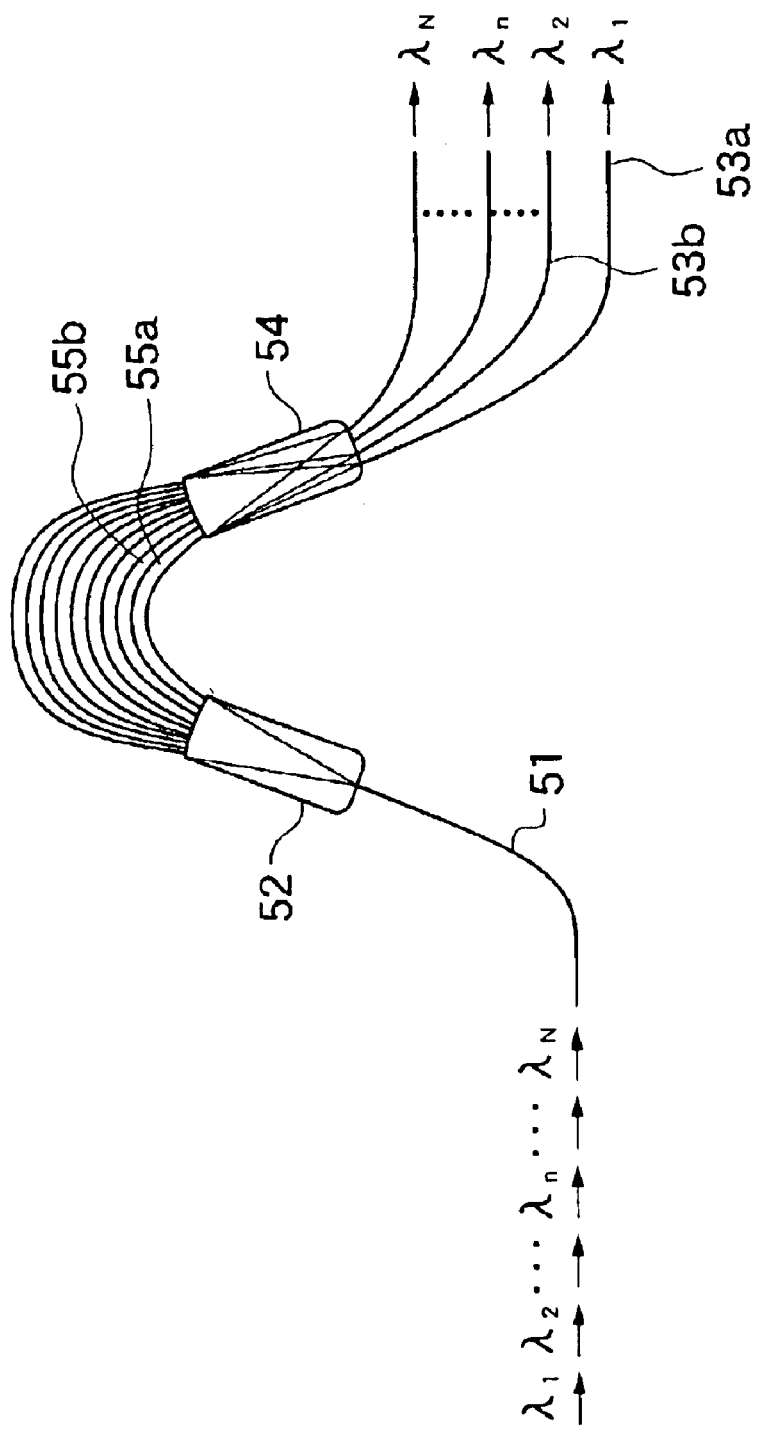
FIG. 2 is a view showing a constitution of an AWG spectrum-separating element.

Alternatively, an AWG (array waveguide grating) spectrum-separating element may be used as the spectrum-separating element 15. FIG. 2 shows a constitution of the AWG spectrum-separating element.

Generally, an array waveguide grating included in a planar lightwave circuit (PLC) is used as the AWG spectrum-separating element. As shown in FIG. 2, the array waveguide grating comprises an input side slab waveguide 52, an output side slab waveguide 54, and a plurality of array waveguides 55a, 55b, . . . , which have a constant difference between their waveguide lengths. An input waveguide 51 is connected to the input side slab waveguide 52, a plurality of output waveguides 53a, 53b, . . . are connected to the output side slab waveguide 54, and the array waveguides 55a, 55b, . . . connect between the input side slab waveguide 52 and the output side slab waveguide 54.

The input side slab waveguide 52 has the form of a sector with an end of the input waveguide 51 as a center of curvature. The output side slab waveguide 54 also has the form of a sector with ends of the output side waveguides 53a, 53b, . . . as a center of curvature. The array waveguides 55a, 55b, . . . are radially arranged such that each of optical axes thereof passes through both of the centers of curvature of the input side slab waveguide 52 and the output side slab waveguide 54. Thereby, the input side slab waveguide 52 and the output side slab waveguide 54 perform a function equal to lenses.

Incident light having different plural wavelengths $\lambda_1$–$\lambda_N$ enters the input waveguide 51 and is guided to the array waveguides 55a, 55b, . . . by the lens function of the input side slab waveguide 52. A plurality of wavelength components included in the incident light excite in the array waveguides 55a, 55b, . . . and are guided to the output waveguides 53a, 53b, . . . having waveguide lengths corresponding to the respective wavelengths.

Referring to FIG. 1 again, the photodetector 16 detects the plurality of wavelength components spectrum-separated by the spectrum-separating element 15. As the photodetector 16, a two-dimensional photoelectric converter having a plurality of photoelectric converting elements arranged in two-dimensional manner and capable of detecting incident light separately in respective positions is used. A PDA (photo diode array), a MOS sensor, etc. can be used as the two-dimensional photoelectric converter. Alternatively, a programmable two-dimensional sensor such as a CCD (charge coupled device) may be used.

The optical transmission path 13, the spectrum-separating element 15, and the photodetector 16 are disposed such that a component having a predetermined wavelength included in a light beam reflected from a predetermined micro-area of the ultrasonic detecting element enters a predetermined photoelectric converting element of the photodetector 16. In the embodiment, light beams $L_1$, $L_2$, . . . output from the optical fibers $OF_1$, $OF_2$, . . . connected to different areas of the ultrasonic detecting element correspond to the first row, the second row, . . . of the photoelectric converting elements that are arranged in a two-dimensional manner, respectively.

The wavelengths $\lambda_1$, $\lambda_2$, . . . of the spectrum-separated components also correspond to the first column, the second column, . . . of the photoelectric converting elements, respectively. By arranging the optical system as to obtain those correspondences, the signal output from the photoelectric converting element positioned in row n and column m is identified as the component having the wavelength $\lambda_n$ included in the light beam $L_m$ output from the optical fiber $OF_m$.

The collimator lens 17 collimates the light output from the light source 11 and allows the light to enter the beam separator 12. The collimator lens 18 also collimates the light output from the optical fibers $OF_1$, $OF_2$, . . . and allows the light to enter the beam separator 12.

Figure 3:
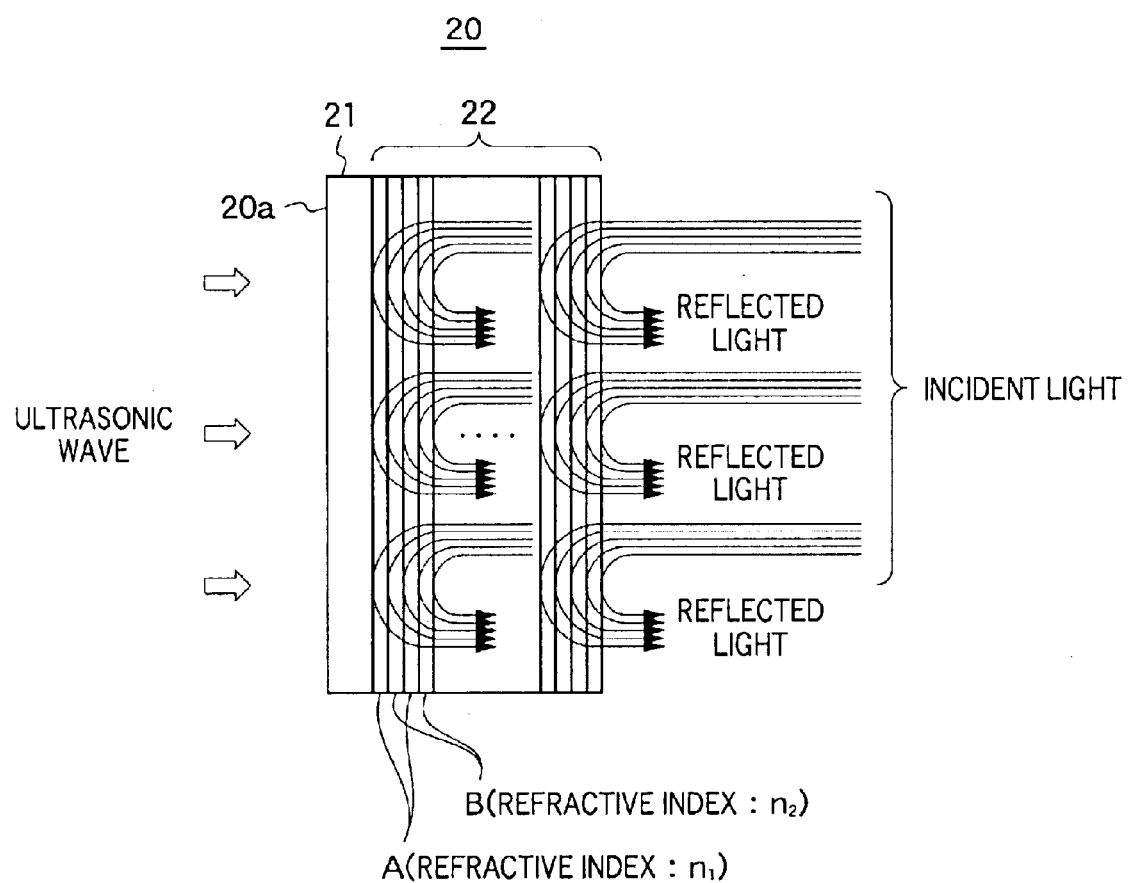
FIG. 3 is an explanatory diagram of a principle of detecting ultrasonic waves by using the ultrasonic detecting element shown in FIG. 1.

Next, referring to FIG. 3, the structure of the ultrasonic detecting element 20 and the detecting principle of an ultrasonic wave will be described in detail. The ultrasonic detecting element 20 is a multi-layered sensor including a substrate 21 and a multi-layered film 22 laminated on the substrate. This multi-layered film 22 constitutes a Bragg grating structure and serves as the ultrasonic sensing portion.

The substrate 21 is a film-like substrate distorted by receiving an ultrasonic wave and has a circular configuration of approximately 2 cm in diameter, for example, or a larger area. Formed on the substrate 21 is the multi-layered film 22 having the Bragg grating structure by alternately laminating two material layers that have different refractive indexes from each other. FIG. 3 shows material layers A having a refractive index $n_1$ and material layers B having a refractive index $n_2$.

Assuming that a pitch (distance) of a periodical structure of the multi-layered film 22 is "d" and that the wavelength of the incident light is "$\lambda$", the reflection condition of Bragg is expressed by the following formula.

$$2d \cdot \sin\theta = m\lambda \quad (1)$$

Herein, "$\theta$" denotes an angle formed between the incidence plane and the incident light and "m" is arbitrary integer number. Assuming that $\theta = \pi/2$, the following formula is held.

$$2d = m\lambda \quad (2)$$

The Bragg grating selectively reflects light having a specific wavelength, which meets the reflection conditions of Bragg, and transmits light having other wavelengths.

When an ultrasonic wave is propagated to the ultrasonic detecting element 20, the detecting element 20 is distorted with the propagation of the ultrasonic wave, and the pitch "d" of the periodical structure changes in the respective positions of the multi-layered film 22. Accordingly, the wavelength "$\lambda$" of the selectively reflected light changes. In the reflection characteristics of the Bragg grating, there is an inclined band, where the optical reflectance changes, in the vicinity of a center wavelength at which the optical reflectance is the highest (i.e., an optical transmittance is lowest). While allowing the light having a center wavelength within the range of the inclined band, to enter the multi-layered film 22, an ultrasonic wave is applied, then, it is possible to observe changes in the intensity of the reflected light (or transmitted light) corresponding to the intensity of the ultrasonic wave in the respective positions on the receiving surface. The two-dimensional strength distribution information of the ultrasonic wave can be obtained by converting the changes in the intensity of the light into the intensity of the ultrasonic wave.

Silica glass (SiO$_2$), optical glass such as BK7 (a product of SCHOTT), etc. is used as the material of the substrate 21. A combination of substances having refractive indexes different by 10% or more from each other is preferred as the substances used for the material layers A and B. For example, a combination of SiO$_2$ and titanium oxide (Ti$_2$O$_3$), a combination of SiO$_2$ and tantalum oxide (Ta$_2$O$_5$), etc. is mentioned. Material layers A and B are formed on the substrate 21 by means of vacuum deposition, sputtering, etc.

In order to reduce the multiple reflection of an ultrasonic wave, it is effective to elongate the distance through which the ultrasonic wave propagates. When the ultrasonic wave propagates, not a little of the ultrasonic wave attenuates. The longer propagation distance results in a larger attenuation amount. Therefore, by ensuring enough propagation distance, it is possible to attenuate the ultrasonic wave satisfactorily before a time point when the ultrasonic wave, which is propagated to one end, is reflected at the other end and returns to the one end. For this purpose, in the embodiment, an optical fiber is used as the optical transmission path, and the received ultrasonic wave is allowed to propagate through the optical fiber. That is, the optical transmission path has both a function to pass the light therethrough and a function as the backing portion for attenuating the ultrasonic wave as well.

Figure 4:
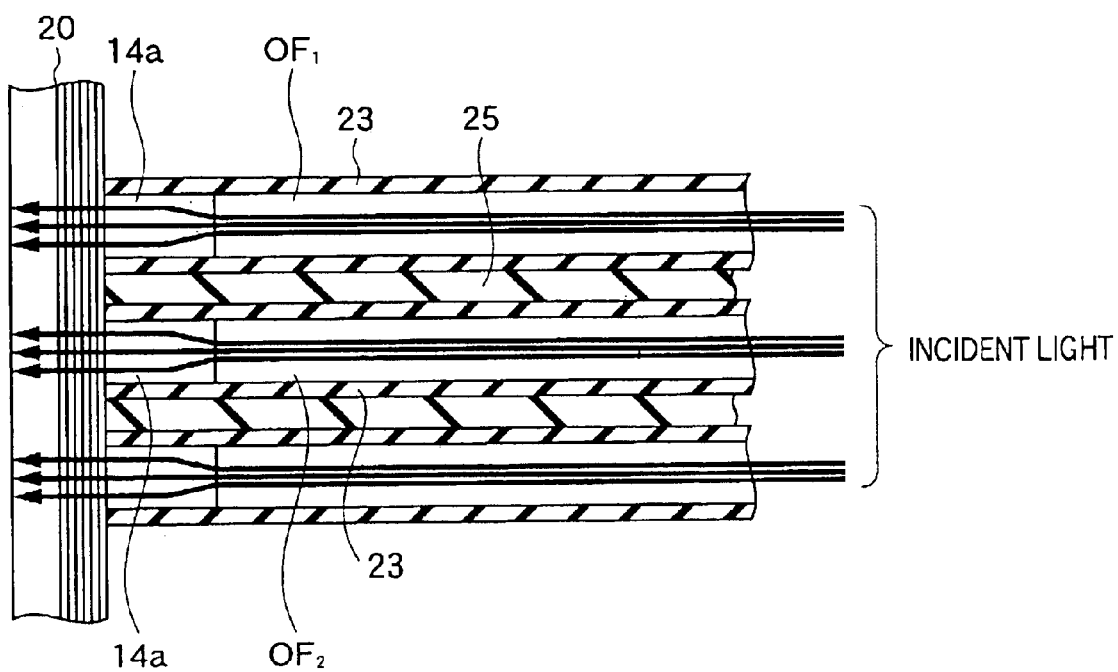
FIG. 4 is an expanded sectional view showing the ultrasonic detecting element, a collimating portion and a connecting portion of an optical transmission path shown in FIG. 1.

FIG. 4 is an expanded sectional view showing a part of optical transmission path 13, the collimating portion 14 and the ultrasonic detecting element 20 shown in FIG. 1. As shown in FIG. 4, the optical fibers OF$_1$, OF$_2$, . . . included in the optical transmission path (bundle fiber) 13 are connected to plural collimator lenses 14a included in the collimating portion (collimator lens array) 14 with optical axes thereof being aligned with each other respectively, and are disposed in a two-dimensional manner and connected to the ultrasonic detecting element 20. The optical fibers OF$_1$, OF$_2$, . . . are bundled by using an adhesive agent 25.

The optical fibers OF$_1$, OF$_2$, . . . are, for example, single mode or multi mode fibers of approximately 2 m in length and are covered with a member (covering material 23) including a resinous material and having a low viscosity. In order to attenuate the ultrasonic wave during the propagation through the optical fiber, the length of 2 m is effective, and propagation energy loss of the ultrasonic wave is further increased by covering the optical fiber with the above member, resulting in earlier ultrasonic wave attenuation.

The light transmitted in the optical fibers OF$_1$, OF$_2$, . . . is diffracted when the light is output from the optical fibers. Accordingly, if the optical fibers OF$_1$, OF$_2$, . . . are connected directly to the ultrasonic detecting element 20, the light is diffused and satisfactory interference is not produced within the ultrasonic detecting element. As a result, the detection sensitivity of the ultrasonic detecting element becomes significantly lower. In order to avoid this phenomenon, the collimator lenses 14a are connected to one ends of the optical fibers OF$_1$, OF$_2$, . . . , respectively, to prevent the output light from being diffused. The collimator lenses 14a collimate the light guided by the respective optical fibers OF$_1$, OF$_2$, . . . with respect to the plural positions on the ultrasonic receiving surface of the ultrasonic detecting element 20.

A gradient index lens (hereinafter, abbreviated to GRIN lens) is used as the collimator lens 14a. The GRIN lens is known as, for example, the product name of Selfoc (registered trademark of NIPPON SHEET GLASS CO., LTD.) lens. The GRIN lens is a gradient refractive index type lens having a refractive index that differs depending on the position, and the optical characteristics thereof changes by changing the length. For example, when the GRIN lens is adapted so that the length thereof is ¼ of a distance between an object and an image (a pitch under which the light focuses erected image), the incident light is output in parallel light.

In the embodiment, Selfoc lens array NA0.46 (a product of NIPPON SHEET GLASS CO., LTD.), in which a number of Selfoc lenses are disposed, is used at a length of 0.25 L (L: a distance between an object and an image), and each Selfoc lens as the collimator lens 14a is connected to the optical fiber.

As shown in FIG. 4, the collimator lenses 14a may be covered with the covering material 23a in order to allow the ultrasonic wave to attenuate earlier as in the case with the optical fibers OF$_1$, OF$_2$, . . . .

The optical fiber and the collimator lens, or, the collimator lens and the ultrasonic detecting element are connected by means of a fusion bond or an adhesive agent. In the case of using an adhesive agent, it is preferred to use a resinous adhesive agent including epoxy series adhesives. In the adhesive agent above, since the acoustic impedance thereof is close to that of the members of the optical fiber and the collimator lens and the substrate of the ultrasonic detecting element, it is possible to prevent the ultrasonic wave from being reflected at each boundary of the respective members during the propagation. It is also preferred to use the resinous adhesive agent including epoxy series adhesives as the adhesive agent 25 for bundling the plurality of optical fibers, because such adhesive agent can attenuate the ultrasonic wave, prevent crosstalk of the ultrasonic wave between the neighboring optical fibers, and maintain the flexibility as a cable. In the embodiment, STYCAST (a product of Emerson & Cuming) is used as the adhesive agent.

Next, the operation of the ultrasonic receiving apparatus according to the embodiment will be described referring to FIGS. 1, 5, and 6A–6C. FIG. 5 is a flowchart showing the operation of the ultrasonic receiving apparatus according to the embodiment.

First, calibration is performed before receiving an ultrasonic wave. Here, the calibration indicates an operation to measure reflection characteristics of the ultrasonic detecting element at any given time and determine wavelength components to be applied as a detection signal. The ultrasonic detecting element is highly sensitive to an ambient environment such as temperature and humidity, the reflection characteristics thereof is changeable. For example, the center wavelength of the reflected light of the ultrasonic detecting element using the Bragg grating changes 0.01 nm/° C. Further, in the ultrasonic detecting element having a two-dimensional detecting surface, there are structural variations in respective micro-areas on the surface. In order to reduce changes in the sensitivity caused by those environmental or structural factors, the calibration is performed in advance.

Note that the calibration may be performed as needed after starting to receive an ultrasonic wave.

Figure 6A:
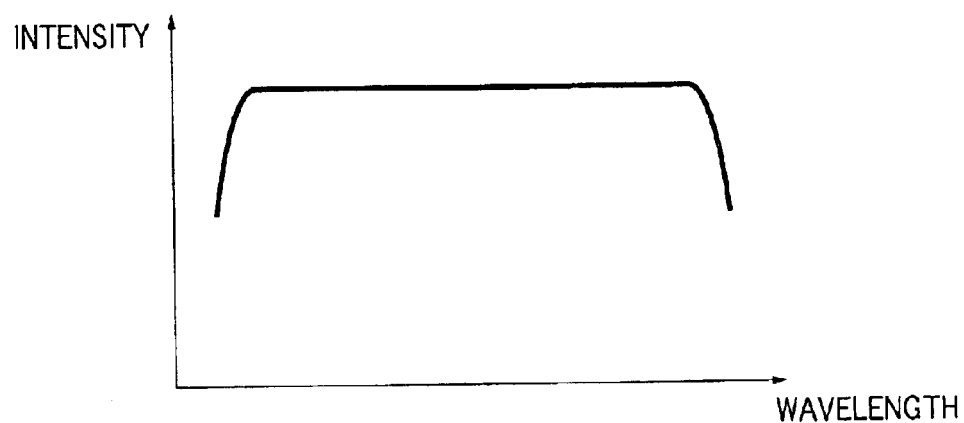
FIGS. 6A–6C are explanatory diagrams of the operation of the ultrasonic receiving apparatus according to the first embodiment of the invention.

At step S1, the ultrasonic receiving apparatus is activated. Accordingly, broadband light having spectrum characteristics shown in FIG. 6A is output from the light source 11. The light output from the light source passes through the collimator lens 17, the beam separator 12, and the collimator lens 18, and enters the optical fibers OF$_1$–OF$_M$ arranged in a line. The light transmitted through each of the optical fibers enters the respective micro-areas of the ultrasonic detecting element 20, and the light reflected in response to reflectance of the respective micro-areas is output from the optical fibers. The light beams L$_1$–L$_M$ output from the optical fibers $OF_1$–$OF_M$ pass through the collimator lens 18 again, are reflected by the beam separator 12 and enter the spectrum-separating element 15. The light beams $L_1$–$L_M$ are spectrum-separated in the spectrum-separating element 15 and the respective wavelength components enter the plural photoelectric converting elements, which are included in respective columns of the photodetector 16, depending on the wavelength.

Accordingly, at step S2, the detection signals of the photoelectric converting elements corresponding to wavelengths $\lambda_1$–$\lambda_N$ are obtained from the respective columns of the photodetector corresponding to the light beams $L_1$–$L_M$.

Figure 6B:
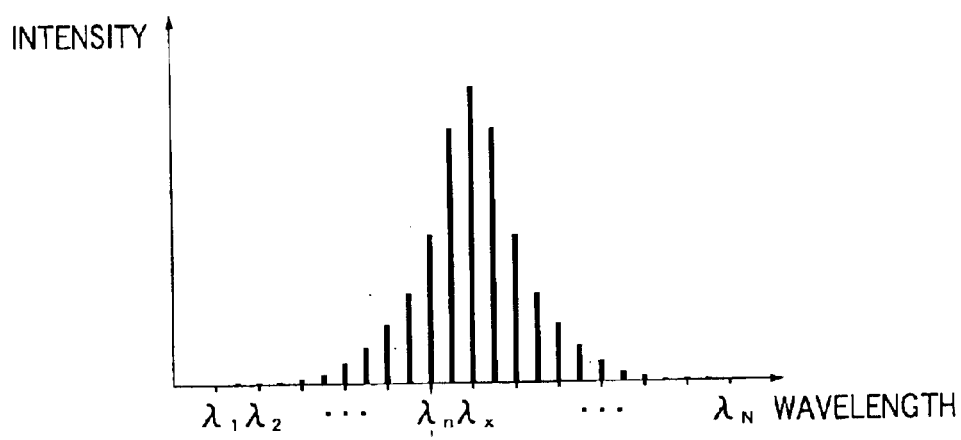

FIG. 6B is a graph obtained on the basis of the detection signal in the photoelectric converting element included in column m of the photodetector 16, and shows a spectral distribution of the light beam $L_m$ that has passed through the optical fiber $OF_m$ and is reflected from the corresponding micro-area of the ultrasonic detecting element. As shown in FIG. 6B, the light beam $L_m$ has the highest intensity at the wavelength $\lambda_x$, where the light beam $L_m$ is selectively reflected under the reflection condition of Bragg.

Figure 6C:
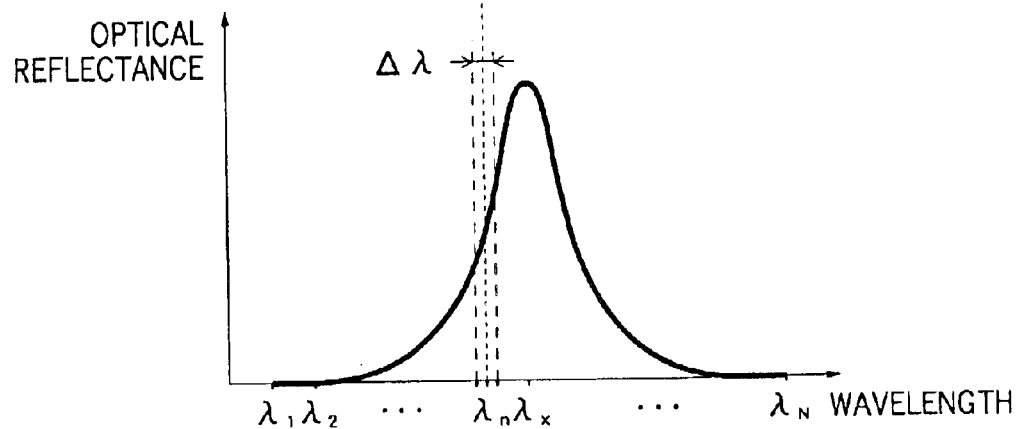

FIG. 6C shows the reflection characteristics of the Bragg grating in the micro-area corresponding to the light beam $L_m$ in the ultrasonic detecting element. As described above, in the reflection characteristics of the Bragg grating, there is an inclined band $\Delta\lambda$ where the reflectance changes steeply in the vicinity of the center wavelength $\lambda_X$ at which the reflectance is the highest (i.e., the transmittance is lowest). When observing the changes in the Bragg grating structure by applying an ultrasonic wave, large changes in intensity are observed in the spectrum-separated area of the inclined band $\Delta\lambda$. This is shown by $\lambda_n$ in FIGS. 6B and 6C.

Therefore, with respect to the micro-area corresponding to the light beam $L_m$ in the ultrasonic detecting element, the light having spectrum-separated area with the wavelength $\lambda_n$ as the center wavelength shows largest changes in intensity. That is, with respect to the optical fiber $OF_m$, it is possible to obtain the highest detection sensitivity by using the signal from the photoelectric converting element (n, m) entered by the component of wavelength $\lambda_n$ in the column m of the photodetector as the detection signal of the ultrasonic wave.

Similarly, it is possible to obtain the highest detection sensitivity in respective micro-areas of the ultrasonic detecting element 20, if the photoelectric converting elements are selected from respective columns entered by the light beams $L_1$, $L_2$, ... output from the $OF_1$, $OF_2$, ..., and the signals output from the selected elements are used as the detection signals of the ultrasonic wave.

Referring to FIG. 5 again, at step S3, the photoelectric converting elements to be used are selected from the respective columns of the photodetector 16 on the basis of results of the calibration.

Next, the receiving operation of an ultrasonic wave is performed.

At step S4, the ultrasonic receiving apparatus is activated. Accordingly, the broadband light output from the light source enters the micro-areas of the ultrasonic detecting element 20 via the optical fibers $OF_1$–$OF_M$. The light beams $L_1$–$L_M$ reflected from the respective micro-areas are spectrum-separated in the spectrum-separating element 15 and enter the photodetector 16.

In this state, the ultrasonic wave is applied to the ultrasonic detecting element 20 (step S5). Then, the pitch of the periodical structure changes in the respective micro-areas of the ultrasonic detecting element 20, and the detection signals output from the photoelectric converting elements selected at step S3 show large changes in intensity.

Next, at step S6, the detection signals output from the photoelectric converting elements selected at step S3 are obtained. Further, processing of these detection signals are performed and the changes in the intensity of the reflected light are converted into the intensity of the ultrasonic wave. Thereby, the intensity of the ultrasonic wave received in the respective micro-areas of the ultrasonic detecting element can be measured in a two-dimensional state.

Figure 7:
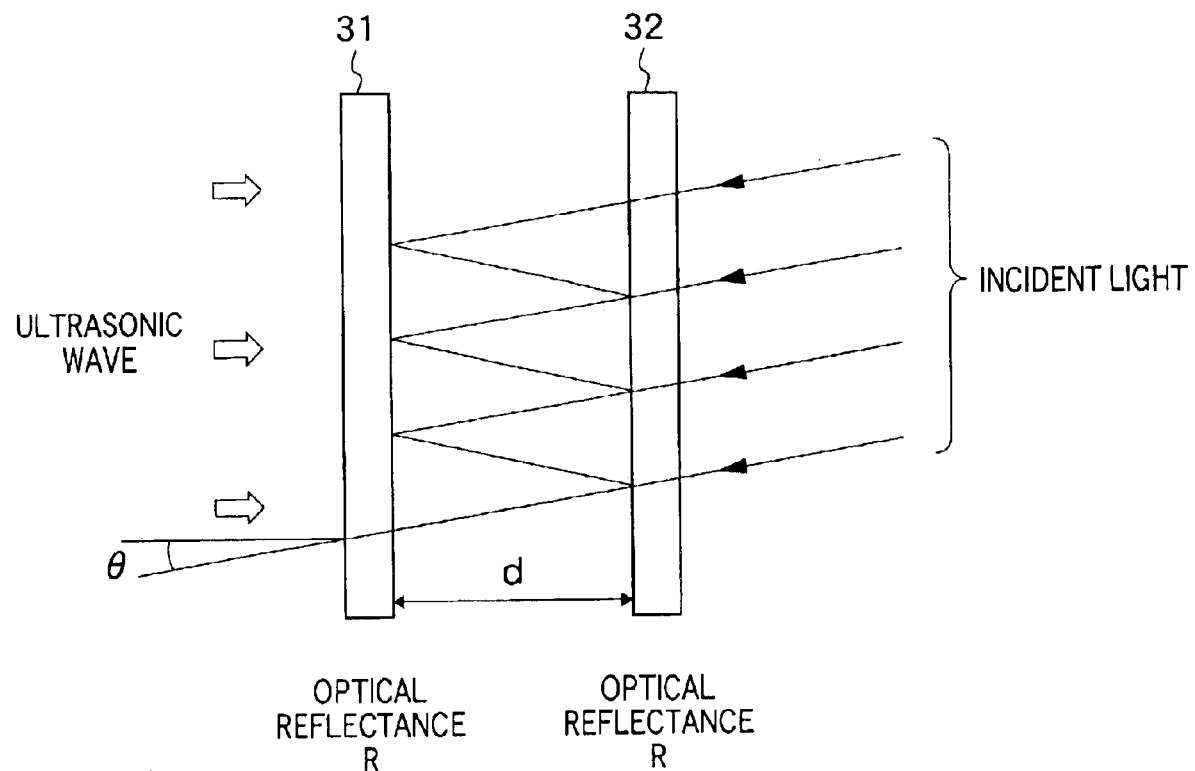
FIG. 7 is a view showing a modification of the ultrasonic receiving apparatus according to the first embodiment of the invention.

Referring to FIG. 7, an example of modification of the first embodiment will be described. In this example, in place of the ultrasonic detecting element 20 in FIG. 1, an ultrasonic detecting element (etalon sensor) 30 as shown in FIG. 7 is used. The constitution other than the above is the same as that described referring to FIGS. 1 and 4.

As shown in FIG. 7, a substrate 31 is a film-like substrate that is deformed by an ultrasonic wave. A substrate 32 is disposed facing to the substrate 31, and these substrates form a structure the same as an etalon.

Assuming that an optical reflectance of the substrates 31 and 32 is "R", a distance between these substrates is "d", and a wavelength of the incident light is "λ", an optical transmittance of the etalon is expressed as the following:

$$T = \{1 + 4R/(1-R)^2 \cdot \sin^2(\phi/2)\}^{-1} \quad (3)$$

$$\phi = 2\pi/\lambda \cdot 2nd \cdot \cos\theta \quad (4)$$

Herein, "θ" is an exit angle measured from the perpendicular line with respect to the exit plane, and "n" is an arbitrary integer number. Assuming that θ=0, the following formula is held.

$$\phi = 4\pi nd/\lambda \quad (5)$$

The etalon transmits the light having wavelength "λ" at an optical transmittance T, and reflects the same at an optical reflectance R=(1−T).

When an ultrasonic wave is propagated to the ultrasonic detecting element 30, since the substrate 31 is distorted and the distance "d" between the substrates 31 and 32 changes in the respective positions on the receiving surface, the reflectance with respect to the light having the wavelength "λ" changes. Here, similarly to the steps described by referring to FIG. 5, a detection is performed in advance and the photoelectric converting elements entered by light having a center wavelength in a region, where the optical reflectance largely changes, are selected in the photodetector, and an ultrasonic wave is applied to the substrate 31 while allowing broadband light to enter. Thereby, it is possible to observe changes in the intensity of the reflected light in response to the intensity of the ultrasonic wave at the respective positions on the receiving surface. By converting the changes in the intensity of the reflected light into the intensity of the ultrasonic wave, the intensity of the ultrasonic wave can be measured in a two-dimensional state.

Figure 8A:
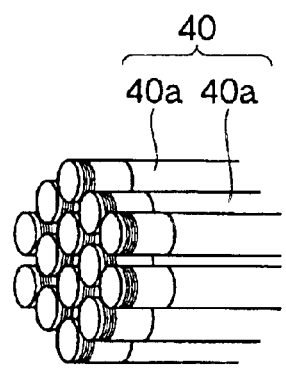
FIGS. 8A and 8B are diagrams showing parts of an ultrasonic receiving apparatus according to a second embodiment of the invention.

Next, referring to FIGS. 8A and 8B, an ultrasonic receiving apparatus according to a second embodiment of the invention will be described. In the second embodiment, in place of the ultrasonic detecting element 20, the optical transmission path 13 and the collimating portion 14 shown in FIG. 1, a bundle fiber 40 having an ultrasonic sensing portion is used as shown in FIG. 8A. The constitution other than the above is the same as that of the first embodiment.

Figure 8B:
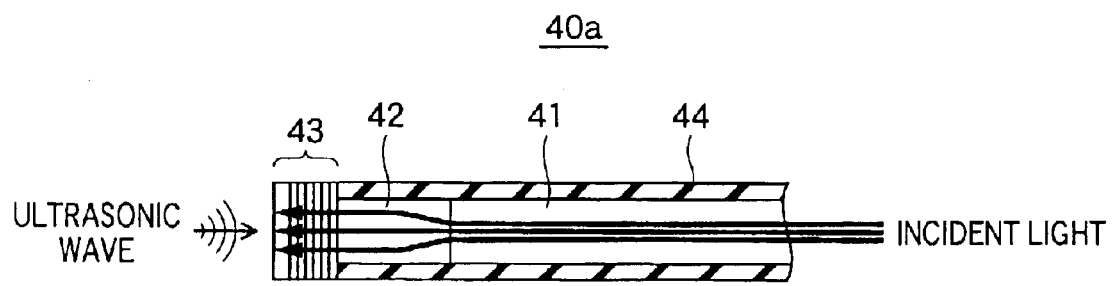

FIG. 8B shows a constitution of a fiber 40a included in the bundle fiber 40. The fiber 40a includes an optical fiber 41 and a collimator lens 42. In the embodiment, a Selfoc lens of 0.25 L in length is used as the collimator lens 42, same as the case of the first embodiment. Further, the both of the above are connected to each other by means of a fusion bond or a resinous adhesive agent including epoxy series adhesives.

Formed at one end of the collimator lens 42 is a multi-layered film 43 in which two different material layers are laminated alternately. The multi-layered film 43 constitutes a Bragg grating structure and serves as the ultrasonic sensing portion. As a material for the multi-layered film 43, for example, a combination of $SiO_2$ and titanium oxide ($Ti_2O_3$), a combination of $SiO_2$ and tantalum oxide ($Ta_2O_5$), etc. is used. The material layer as described above has been formed on the collimator lens 42 by means of vacuum deposition, sputtering or the like.

The fiber 40a is covered by a member (covering material 44) having a low viscosity so that an ultrasonic wave is attenuated before the ultrasonic wave, which is propagated to one end of the fiber 40a, is reflected at the other end thereof. Further, as shown in FIG. 8B, the covering material 44 may also cover the collimator lens 42. Therefore, since the energy loss of the ultrasonic wave propagated to the fiber 40a can be made larger, an effect as a backing portion can be increased by allowing the ultrasonic wave to attenuate earlier.

The bundle fiber 40 having the ultrasonic sensing portion is manufactured by bundling a number of such fibers 40a as described above using a resinous adhesive agent including epoxy series adhesives.

In the above-described first and second embodiments, the ultrasonic wave sensing performance can be increased by adding a light amplifier. Referring to FIG. 9, this modification will be described below.

In an ultrasonic receiving apparatus shown in FIG. 9, at least one of a light amplifier 91 and a light amplifier 92 is added to the ultrasonic receiving apparatus shown in FIG. 1. The light amplifier 91 is disposed between the collimator lens 17 and the beam separator 12, amplifies the parallel light entered from the collimator lens 17, and outputs the light to the beam separator 12. On the other hand, the light amplifier 92 is disposed between the beam separator 12 and the spectrum-separating element 15, amplifies the light entered from the beam separator 12, and outputs the amplified light to the spectrum-separating element 15.

As the light amplifier, for example, an optical fiber amplifier doped with Erbium (Er), that is, EDFA (Er-doped optical fiber amplifier) is used. The EDFA is capable of increasing intensity of light by approximately one to two orders.

When the light amplifier is disposed between the light source 11 and the ultrasonic detecting element 20, the intensity of the incident light entering the ultrasonic detecting element 20 is amplified. Alternatively, when the light amplifier is disposed between the ultrasonic detecting element 20 and the photodetector 16, although the intensity of the incident light entering into the ultrasonic detecting element 20 is not changed, the intensity of the reflected light that enters into the photodetector 16 is amplified. In this case, the changes in the intensity of the reflected light that has been modulated by the received ultrasonic wave are also amplified.

In any case, since the amount of the reflected light that enters the photodetector 16 is increased by amplifying the intensity in the state of light, the influence of electrical noise in the photodetector 16 are reduced resulting in an increased SN-ratio of the ultrasonic receiving apparatus. Further, in the case where the both of the light amplifiers are used simultaneously, the SN-ratio can be more increased.

Figure 10:
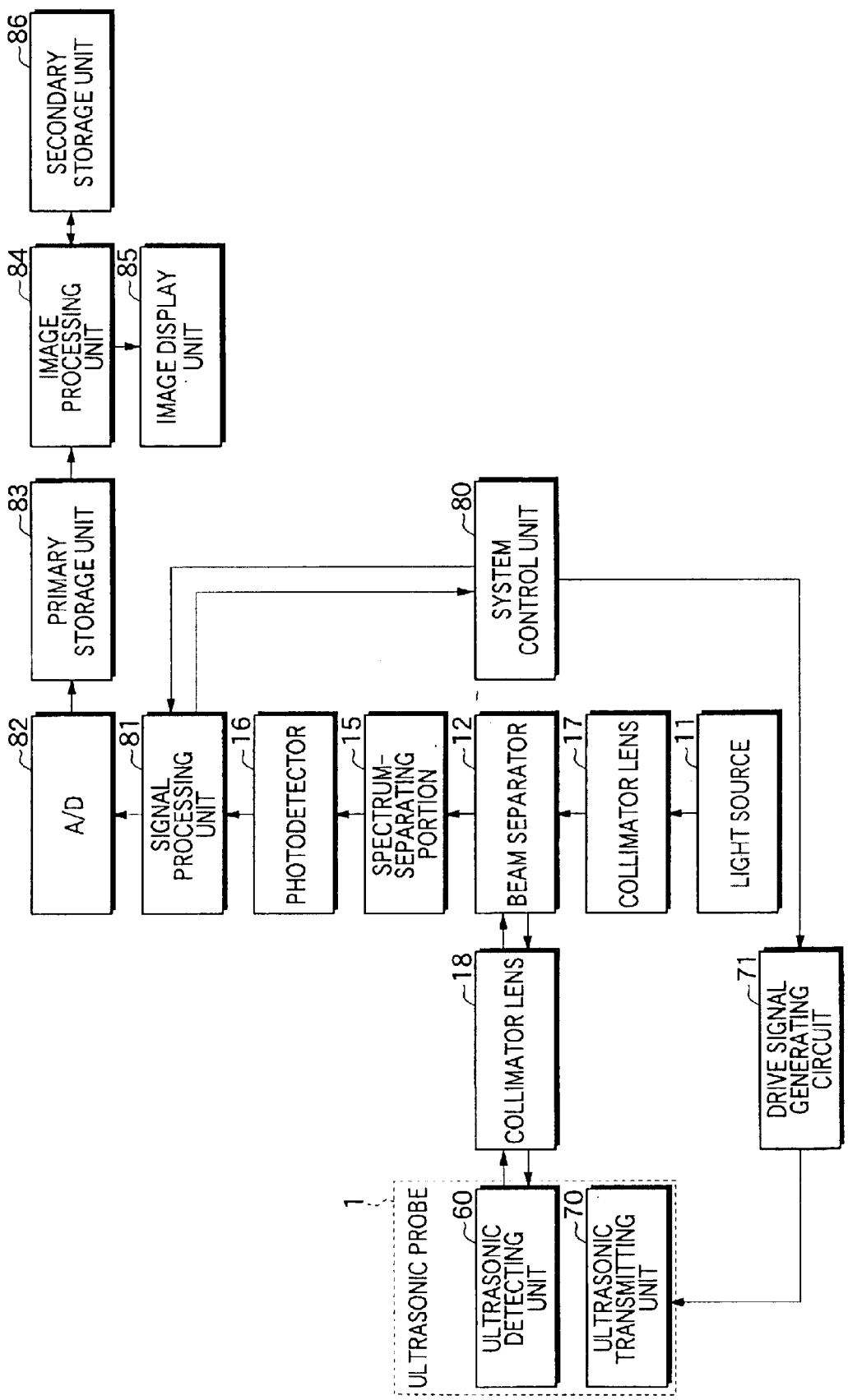
FIG. 10 is a block diagram showing an ultrasonic imaging apparatus applying the ultrasonic receiving apparatus according to the invention.

Referring to FIG. 10, an ultrasonic imaging apparatus applying the ultrasonic receiving apparatus according to the first or the second embodiment, will be described.

An ultrasonic detecting unit 60 shown in FIG. 10 includes the ultrasonic detecting element in the first or the second embodiment and is connected to the lens 18 and the beam separator 12 via the collimating portion and the optical transmission path.

The ultrasonic imaging apparatus also includes an ultrasonic transmitting unit 70 and a drive signal generating circuit 71. The ultrasonic transmitting unit 70 transmits an ultrasonic wave on the basis of a drive signal generated by the drive signal generating circuit 71. The ultrasonic transmitting unit 70 comprises, for example, an oscillator made by forming electrodes on a piezoelectric element. The piezoelectric element includes a piezoelectric ceramic represented by PZT (Pb (lead) zirconate titanate), materials having piezoelectric properties represented by a macromolecule piezoelectric element such as PVDF (polyvinylidene difluoride), etc. Applying a voltage to the electrodes of the oscillator by transmitting an electrical pulse signal or a continuous wave electrical signal, the piezoelectric element expands and constructs due to a piezoelectric effect. Thereby, an ultrasonic pulse or a continuous ultrasonic wave is generated from the oscillator.

The ultrasonic wave transmitted from the ultrasonic transmitting unit 70 is reflected by an object to be inspected and is received by the ultrasonic detecting unit 60. At this time, the ultrasonic sensing portion of the ultrasonic detecting unit 60 expands and contracts according to the ultrasonic wave received on the receiving surface, and the optical reflectance of the ultrasonic sensing portion changes in response to the expansion and contraction. On the other hand, the light generated by the light source and has passed through the beam separator 12 enters the ultrasonic detecting unit 60. The light is subjected to an intensity modulation owing to the changes in the optical reflectance in the ultrasonic detecting unit 60, and reflected. The reflected light enters the spectrum-separating element 15 via the collimator lens 18 and the beam separator 12, is spectrum-separated, and then enters the photodetector 16.

Further, the ultrasonic imaging apparatus includes a system control unit 80, a signal processing unit 81, an A/D converter 82, a primary storage unit 83, an image processing unit 84, an image display unit 85, and a secondary storage unit 86.

A detection signal output from a predetermined photoelectric converting element of the photodetector 16 is subjected to processing such as phase adjustment, logarithmic amplification, and demodulation in the signal processing unit 81, and further, is converted into a digital signal in the A/D converter 82.

The primary storage unit 83 stores data on a plurality of planes based on the converted data. The image processing unit 84 reconstitutes two-dimensional data or three-dimensional data based on the data, and carries out processing such as interpolation, response modulation processing, and tone processing. The image display unit 85 is a display apparatus such as a CRT or an LCD, and displays images based on the processed image data. Further, the secondary storage unit 86 stores data processed in the image processing unit 84.

The system control unit 80 controls the drive signal generating circuit 71 to generate a drive signal in predetermined timing, and controls the signal processing unit 81 to take in the detection signal output from the photodetector 16 after a predetermined time has passed from the time of transmission. Thus, it is possible to detect the ultrasonic wave reflected from a specific depth of the object by controlling the drive signal and detection signal to limit time periods for reading. In addition, the system control unit 80 controls the signal processing unit 81 to obtain reflection characteristics in the plural detection areas of the ultrasonic detecting unit 60 on the basis of the detection result of the photodetector 16 at the time of calibration, select one set of photoelectric converting elements to be used for detecting the ultrasonic wave from the plural photoelectric converting elements of the photodetector 16 on the basis of the reflection characteristics, and use the signals output from the selected one set of the photoelectric converting elements as the detection signals when receiving the ultrasonic wave.

Here, the ultrasonic detecting unit 60 and the ultrasonic transmitting unit 70 may be provided separately, or an ultrasonic probe 1 may be composed of a combination of the ultrasonic transmitting unit 70 and the ultrasonic detecting element.

As described above, according to the invention, since the reflection characteristics of the ultrasonic detecting element are obtained by the calibration, and the photoelectric converting element to be used for detection is selected on the basis of the reflection characteristics, if the reflection characteristics changes under environment such as temperature and humidity, it is possible to maintain a high detection sensitivity. Further, it is similarly possible to reduce the variation of the sensitivity in respective detection areas of the ultrasonic detecting element. Furthermore, since broadband light is used and the wavelength used for detection is selected from the spectrum-separated light, it is not required to control the wavelength of the light according to the environment and the detection area or change the reflection characteristics according to the respective detection areas. Thereby, it is possible to miniaturize the ultrasonic receiving apparatus by simplifying its constitution. Thus, manufacturing of the ultrasonic receiving apparatus becomes easy and the cost can be reduced.

What is claimed is:

1. An ultrasonic receiving apparatus comprising:
   a light source for generating broadband light;
   an ultrasonic detecting element including an ultrasonic sensing portion which is expanded and contracted by a received ultrasonic wave to change an optical reflectance thereof in accordance with expansion and contraction thereby performing intensity modulation of the light generated by said light source;
   spectrum separating means for spectrum-separating the light intensity-modulated by said ultrasonic detecting element; and
   photo detecting means having a plurality of photoelectric converting elements for detecting the light spectrum-separated by said spectrum separating means for each of plural wavelength components.

2. The ultrasonic receiving apparatus according to claim 1, further comprising:
   an optical transmission path for transmitting the light between said ultrasonic detecting element and said spectrum separating means.

3. The ultrasonic receiving apparatus according to claim 2, wherein:
   said ultrasonic detecting element has a plurality of detection areas each for detecting an ultrasonic wave;
   said spectrum separating means spectrum-separates a plurality of light beams guided from the plurality of detection areas of said ultrasonic detecting element in bulk; and
   said photo detecting means detects the plurality of light beams spectrum-separated by said spectrum separating means for each of plural wavelength components.

4. The ultrasonic receiving apparatus according to claim 3, further comprising:
   control means for obtaining relationship between wavelengths and reflection intensity of the light in the plurality of detection areas of said ultrasonic detecting element on the basis of a detection result of said photo detecting means at a calibration mode to select a set of photoelectric converting elements to be used for detecting an ultrasonic wave from among the plurality of photoelectric converting elements of said photo detecting means on the basis of the relationship, and controlling a signal processing unit to use signals output from the selected set of photoelectric converting elements as detection signals at a receiving mode.

5. The ultrasonic receiving apparatus according to claim 1, wherein:
   said ultrasonic detecting element has a plurality of detection areas each for detecting an ultrasonic wave;
   said spectrum separating means spectrum-separates a plurality of light beams guided from the plurality of detection areas of said ultrasonic detecting element in bulk; and
   said photo detecting means detects the plurality of light beams spectrum-separated by said spectrum separating means for each of plural wavelength components.

6. The ultrasonic receiving apparatus according to claim 5, further comprising:
   control means for obtaining relationship between wavelengths and reflection intensity of the light in the plurality of detection areas of said ultrasonic detecting element on the basis of a detection result of said photo detecting means at a calibration mode to select a set of photoelectric converting elements to be used for detecting an ultrasonic wave from among the plurality of photoelectric converting elements of said photo detecting means on the basis of the relationship, and controlling a signal processing unit to use signals output from the selected set of photoelectric converting elements as detection signals at a receiving mode.

7. An ultrasonic receiving method comprising the steps of:
   (a) allowing light to enter an ultrasonic detecting element including an ultrasonic sensing portion which is expanded and contracted by a received ultrasonic wave to change an optical reflectance thereof in response to the expansion and contraction thereby performing intensity modulation of the incident light, spectrum-separating the light intensity-modulated in a plurality of detection areas of said ultrasonic detecting element and detecting the spectrum-separated light for each of plural wavelength components by using photo detecting means having a plurality of photoelectric converting elements so as to obtain relationship between wavelengths and reflection intensity of the light in a plurality of detection areas of an ultrasonic detecting element;
   (b) selecting a set of photoelectric converting elements to be used for detecting an ultrasonic wave from among the plurality of photoelectric converting elements of said detecting means on the basis of the relationship obtained at step (a); and
   (c) allowing light to enter said ultrasonic detecting element when receiving the ultrasonic wave, outputting the light intensity-modulated by a received ultrasonic wave in said ultrasonic detecting element into different directions depending upon the wavelengths thereof and detecting the light for each of plural wavelength components by using the set of photoelectric converting elements selected at step (b) so as to obtain information on the ultrasonic wave received in the plurality of detection areas of said ultrasonic detecting element.

* * * * *